Dec. 26, 1961 E. S. BOERNER Plant Pat. 2,115
ROSE PLANT
Filed Feb. 7, 1961
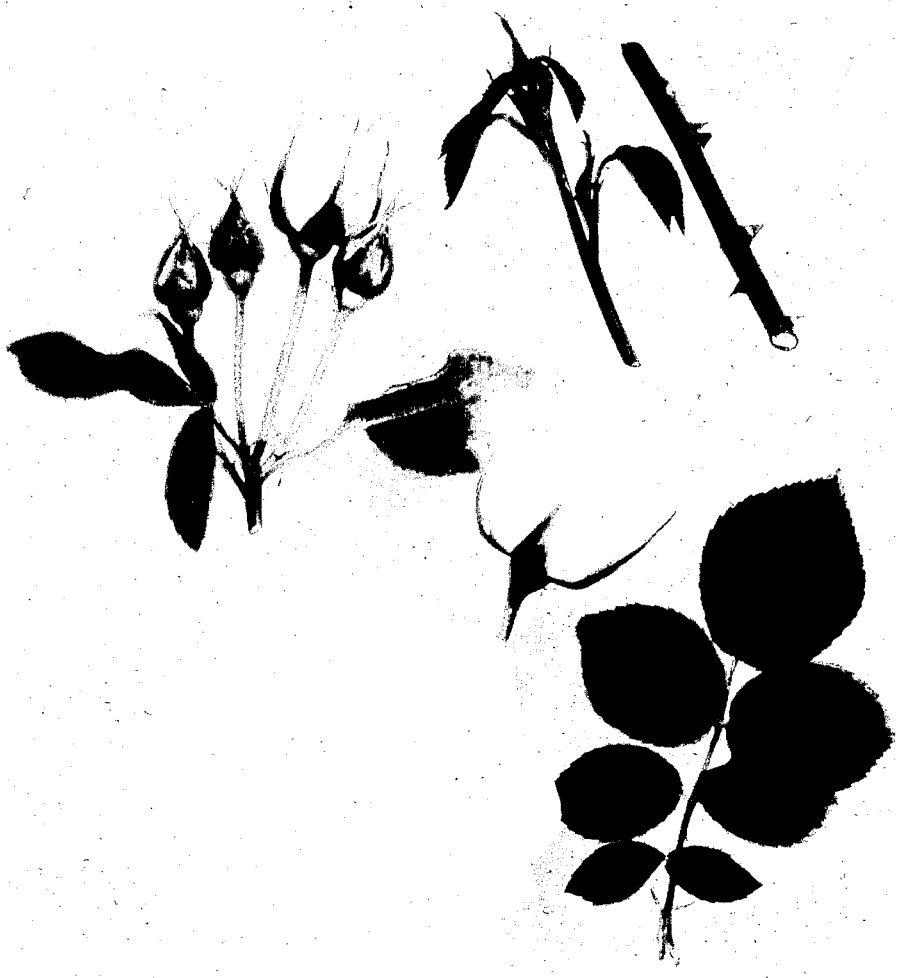
Inventor.
E. S. Boerner
By: Robb & Robb
Attorneys.

United States Patent Office

Plant Pat. 2,115
Patented Dec. 26, 1961

2,115
ROSE PLANT

Eugene S. Boerner, Newark, N.Y., assignor, by mesne assignments, to Home Nursery Products Corporation, Newark, N.Y., a corporation of New York Filed Feb. 7, 1961, Ser. No. 87,727
1 Claim. (Cl. 47—61)

The present invention relates to a new and distinct variety of rose plant of the floribunda class, which was originated by me by crossing the floribunda variety named "Princess White" (Plant Patent No. 1,540) with the hybrid tea variety named "Golden Masterpiece" (Plant Patent No. 1,284).

The primary objective of this breeding was to produce a new floribunda rose variety which bears larger and more stiff-petaled and longer lasting flowers. This objective was fully achieved, along with other desirable improvements, as evidenced by the following unique combination of characteristics which are outstanding in the new variety and which distinguish it from its parents, as well as from all other varieties of which I am aware:

(1) A free and continuous blooming habit;
(2) Large, stiff-petaled flowers;
(3) Long lasting flower qualities; and
(4) A distinctive clean White general color tonality of the flowers which lasts throughout the blooming period.

A sexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Princess White."
*Pollen parent.*—"Golden Masterpiece."
Classification:
*Botanic.*—Floribunda.
*Commercial.*—Floribunda.

*Flower*

(Observations made from specimens grown outdoors at Newark, New York, near mid-afternoon and during the first half of the month of August.)
Blooming habit: Recurrent—continuous; free.
Bud:
*Size.*—Medium.
*Form.*—Ovoid; is not affected by wet or hot weather.
*Color.*—When sepals first divide—Lumiere Green, Plate 17. When petals begin to unfurl—White, 53, lightly overcast with Sea-Foam Yellow, Plate 31. When half-blown: inside of petals—White, Plate 53, with lower half of petals lightly overcast with Pale Chalcedony Yellow, Plate 17; reverse of petals—White, Plate 53, with base of petals Picric Yellow, Plate 4.
*Sepals.*—Slightly branched; curl back when petals begin to unfurl. Color: inside—Turtle Green, Plate 32; outside—Bice Green, Plate 17.
*Calyx.*—Color—Bice Green, Plate 17. Shape—pear. Size—Small. Aspect—smooth. Odor when rubbed—none.

*Peduncle.* — Length — medium. Aspect — rough. Strength—erect; slender. Color—Lettuce Green, Plate 5.
*Opening.*—Opens up well; is not affected by adverse weather conditions.
Bloom:
*Size.*—Large. Average size when fully expanded—4½ inches.
*Borne.*—Both singly and several together.
*Stems.*—Medium length; strong.
*Form (when first open).*—Cupped. Permanence—retains its form to the end.
*Petalage.*—Double (full but open center). Number of petals under normal conditions—from 30 to 35.
*Color.*—Center of flower—White, Plate 53, with lower half of petals lightly overcast with Pale Chalcedony Yellow, Plate 5. Outer petals—White, Plate 53. Base of petals (aiglet)—Light Chalcedony Yellow, Plate 5. Inside of petals—White, Plate 53. Reverse of petals—White, Plate 53. General tonality from a distance—White, Plate 53.
*Discoloration.*—General tonality at end of first day—White, Plate 53. Second day—White, Plate 53. Third day—White, Plate 53.
Petals:
*Texture.*—Leathery; stiff; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Strontian Yellow, Plate 16.
Stamens, filaments (threads): Long. Color—Sulphur Yellow, Plate 5.
Pollen: Color—Barium Yellow, Plate 16.
Styles: Bunched; uneven length; medium length; thin.
Stigmas: Color—Naphthalene Yellow, Plate 16.
Ovaries: Some protruding from calyx.
Hips: None.
Seeds: None.

*Plant*

Form: Bush.
Growth: Vigorous; branching.
Foliage: Compound of 3–5 leaflets.
*Size.*—Medium.
*Quantity.*—Abundant.
*Color.*—New foliage: upper side—Courge Green, Plate 17, with outer edge of leaves overcast with Oxblood Red, Plate 1; under side—Acajou Red, Plate 13, with midrib of Mignonette Green, Plate 31. Old foliage: upper side—Varley's Green, Plate 18; under side—Light Bice Green, Plate 17.
*Shape.*—Oval pointed.
*Texture.*—Upper side—leathery. Under side—smooth.
*Ribs and veins.*—Ordinary.
*Edge.*—Serrated (saw-toothed).
*Serration.*—Single; small.
*Leaf stem.*—Color—Bice Green, Plate 17. Under side—smooth.
*Stipules.*—Long; bearded.

Wood:

*New wood.*—Color—Yellowish Oil Green, Plate 5. Bark—smooth.

*Old wood.*—Color—Cedar Green, Plate 6. Bark—smooth.

Thorns:

*Thorns.*—Quantity: on main stalks from base—ordinary; on laterals from stalk—ordinary. Form—flat base; medium length; straight. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a free and continuous blooming habit, large, stiff-petaled flowers, long-lasting flower qualities, and a distinctive clean White general color tonality of the flowers which lasts throughout the blooming period.

No references cited.